United States Patent [19]

Stone

[11] 4,136,159

[45] Jan. 23, 1979

[54] RADIOASSAY OF FOLATES

[75] Inventor: Marcia J. Stone, Wellesley, Mass.

[73] Assignee: New England Nuclear Corporation, Boston, Mass.

[21] Appl. No.: 772,841

[22] Filed: Feb. 28, 1977

[51] Int. Cl.[2] ...................... G01N 33/16; A61K 43/00

[52] U.S. Cl. ...................................... 424/1; 23/230 B; 206/569; 424/12; 544/257

[58] Field of Search .............................. 429/1, 1.5, 12; 23/230 B; 260/251.5, 112 R; 206/569

[56] References Cited

U.S. PATENT DOCUMENTS

| | | | |
|---|---|---|---|
| 3,972,991 | 8/1976 | Caston et al. | 23/230 B X |
| 3,989,812 | 11/1976 | Barrett et al. | 23/230 B X |
| 3,998,431 | 10/1976 | Givas et al. | 424/1 |
| 4,021,535 | 5/1977 | Polito | 424/1 |

OTHER PUBLICATIONS

Edwards et al., International A., pp. 31-40 , 1974.
Nars et al., Endocrinology, vol. 57, XLVII (1973).
Gilby et al., Journal of Endocrinology, vol. 58, XII, (1973).
Cameron et al., Steroid Immunoassay, Apr. 1974, pp. 153-176.
Hunter et al., Steroid Immunoassay, Apr. 1974, pp. 141-152.
Gupta (Ed.), Verlag Chemie, GmbH, D-6940, Weinheim, 1975, pp. 185-195.

*Primary Examiner*—Leland A. Sebastian
*Assistant Examiner*—Christine M. Nucker
*Attorney, Agent, or Firm*—Sewall P. Bronstein

[57] ABSTRACT

Novel folic acid derivatives useful in processes for analysis of biological fluids for folic acid or its metabolites comprising components of the formula:

OH
$CH_2$—NH—⟨benzene⟩—CO—
$H_2N$ N N N N
—NH—CH—$CH_2$—$CH_2$—CO—NH
COOH $CH_2$
$CH_2$
N R
N wherein R is hydrogen or radioactive iodine.

32 Claims, No Drawings

RADIOASSAY OF FOLATES

BACKGROUND OF THE INVENTION

This invention relates to novel folic acid derivatives useful for determining the amounts of folic acid and its metabolites in biological or other liquids by radioassay, and to methods of analyzing such biological liquids using the materials disclosed herein.

The usefulness of serum and red cell folate assays in the diagnosis of nutritional anemias and related illnesses is now well established. Some of the primary conditions where folate levels have diagnostic significance include nutritional deficiencies, especially in cases of severe alcoholism, and a variety of malabsorption syndromes including functional damage to the upper third of the small bowel, pregnancy, and a number of types of megaloblastic anemia. Folic or pteroylglutamic acid as such is not biologically active in man. This material undergoes conversion in the body, and the dominant form in human serum is N,5-methyltetrahydrofolic acid.

Early methods of analyzing endogenous folates involved a microbiological assay using *Lactobacillus casei,* whose growth is dependent on the presence of folic acid and its derivatives in an incubation medium. However, this technique is cumbersome, time consuming, and subject to interference by drugs such as folate antagonists or antibiotics. Recent developments in radioassay techniques have resulted in the development of competitive binding methods for the determination of folates which overcome many of the limitations of the microbiological procedures. The basic principle of such methods is that of competitive protein binding. Basically, advantage is taken of the affinity of folates to specific folate binders, i.e., binders which specifically bind only folates. Suitable binders are known and are obtainable from sources such as cow's milk, hog's kidney, etc. Folate labeled with radioactivity is mixed with the sample to be analyzed and a specific folate binder, and the radioactive labeled folate competes with the unlabeled folates in the sample to be analyzed for binding by the folate-specific binder. As a result, the ratio of bound-labeled folic acid to free-labeled folic acid diminishes as the concentration of unlabeled folate is increased. Accordingly, the concentration of folate in an unknown sample, e.g., a patient's blood serum, is obtained by comparing inhibition of labeled folate binding observed, with that produced by known amounts of folate, as presented in a standard curve. After mixing the labeled folate, the sample and the binder, the bound material, both labeled and unlabeled, is separated from the unbound or "free" material, by any of a variety of known separation techniques, e.g., by adsorption onto charcoal or other known adsorbents, or by precipitation techniques, e.g., using ammonium sulfate or polyethylene glycol or other known precipitants, or by dialysis. The radioactivity in the bound fraction is then measured, the data is plotted on a graph to prepare the standard dose-response curve, and the amount of folate in a sample is determined by interpolation from the standard curve.

Thus, the use of protein binding in folate determination requires the use of a binder, a "tracer," which is a radioactive-labeled material which has the ability to compete with unlabeled material for binding, and a "standard." The standard is the folate material which is added in known specified amounts to the binder and the tracer, in order to obtain the standard curve.

Since the predominant form of folate found in human serum is the reduced 5-methyl derivative of folic acid, early competitive binding techniques utilized the N,5-methyltetrahydrofolic acid as the standard, against which the biological samples would be compared. The tracer used was generally tritiated folic acid, and the binder used was generally one obtained from milk. Such procedures suffered from a number of disadvantages, caused in part by the extreme instability of the N,5-methyltetrahydrofolic acid used as a standard, and also from the disadvantages of using tritium as the labeling radionuclide. Tritium requires cumbersome liquid scintillation counting procedures and is generally unsuitable for radioassay techniques, since its use is subject to a variety of errors. See, Chervu et al., "Radiolabeling of Antigens: Procedures and Assessment of Properties," *Seminars in Nuclear Medicine,* 5:157, 158 (1975). The preferred labeling radionuclide is radioactive iodine, more preferably $^{125}I$. However, incorporation of the large iodine atom into the molecular structure of the material to be analyzed changes that structure, and can have adverse affects on its affinity for the binder. One approach that has been taken to overcome this difficulty is conjugation labeling, in which a molecule labeled with $^{125}I$ is added to (conjugated with) the molecule which is to be determined, in order to make a composite molecule in which the iodine will be removed from the situs of attraction to the binder and will, therefore, not interfere with the affinity of the tracer to the binder.

It is an object of this invention to provide novel folic acid derivatives which are useful in a radioassay for folic acid and its metabolites in biological liquids.

It is a further object of this invention to provide a method of radioassaying for folic acid and its metabolites in biological liquids, using novel folic acid derivatives.

It is a further object of this invention to provide a method for radioassaying which is easy, inexpensive, and reproducible, yielding labeled tracers having high specific binding activity, specific radioactivity, purity, and extremely long shelf life.

The folic acid derivatives of this invention are conjugates of folic acid with histamine, or with iodinated histamine, and are represented by the following general structural formula:

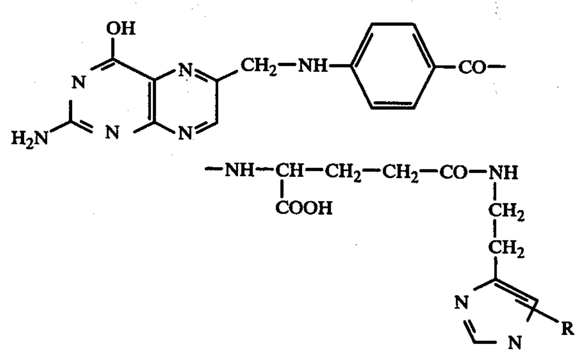

in which R is hydrogen or radioactive iodine, such as $^{125}I$ or $^{131}I$. As is known in the art, it is possible to have a plurality of glutamate linkages attached to the pteroyl moiety, and in such cases the labeled or unlabeled histamine moiety would bond to the pteroyl moiety by such linkages.

In accordance with the present invention, it has been found that the labeled folic acid-histamine conjugate of the present invention is a particularly effective tracer in folic acid determinations by radioassay, and that such tracer has an extremely long shelf life, as compared with other folic acid tracers. This is particularly important, because, although use of radioactive iodine as the labeling radionuclide is highly advantageous from the standpoint of providing higher specific activity, and thus higher sensitivity in shorter counting times, low chemical stability of the tracer compound can substantially irradicate the advantages, from a practical standpoint, since if all of the tracer rapidly chemically degrades, the tracer will no longer compete with the material to be measured for the binder. The folic acid-histamine conjugate of the present invention, although preferably stored at referigerator temperature (2°-8° C.), is so stable that it can be simply stored at room temperature for extended periods without substantial degradation, whereas tritiated folic acid, for example, is unstable to the extent that it must normally be stored away from light and frozen in separate aliquoted tubes, to avoid any thawing and refreezing of unused portions of that tracer.

It has also been discovered that unlabeled folic acid-histamine conjugate can be used to distinct advantage as a standard in the radioassay process for determination of folic acid and its metabolites in biological or other liquids. It is far more stable than N,5-methyltetrahydrofolic acid previously used as a standard, and under suitable conditions gives essentially identical results. Optimal conditions for such use can be easily determined by known methods, e.g., that disclosed in Givas et al., "pH Dependence of the Binding of Folates to Milk Binder in Radioassay of Folates," *Clinical Chemistry,* 21:427-8 (1975), incorporated herein by reference.

The compounds of this invention may be simply prepared by reacting folic acid with histamine in the presence of a coupling reagent, e.g., a a dehydrating reagent such as a carbodiimide, in aqueous medium. Preferably the reaction is conducted at a pH of about 6 to 10, most preferably at a pH of about 7.5 to 9. Suitable coupling reagents include a wide variety of compounds commonly used in coupling procedures in peptide or other syntheses, including dicyclohexyl carbodiimide, 1-ethyl-3-(3-morpholinomethyl) - carbodiimide, N,N'-carbonyldiimidazole, N,N'-carbonyl-5-triazine, bis-5-phenylene pyrophosphite, diethyl chlorophosphonate, diethyl cyanamide, diethyl ethylenepyrophosphite, diphenylketene p-tolylamine, ethoxyacetylene, ethylene chlorophosphite, N-ethyl-5-phenyl-isoxazolium-3'-sulfonate N-hydroxypyridine, N-hydroxyphthalimide, N-hydroxypiperidine, N-hydroxysuccinimide, phenylphosphorodi-(1-imidazolate), and still others will be readily recognized by those skilled in the art. Separation of the folic acid-histamine conjugate from the reaction mixture is by standard chromatographic or other separation techniques.

The molar ratios of histamine to folic acid to coupling reagent may vary over wide ranges, and may generally be from about 1:1:1 to about 3:1:20 or 1:3:20. Preferably the coupling reagent is added in molar excess, being at least 0.1 moles in excess of the lesser of the other two reactants. The reaction can be run at 0° C. to 30° C. and should be permitted to proceed from about 1 to 72 hours, preferably being run for approximately 1 day at room temperature.

Other methods of producing the conjugate willbe readily apparent to those skilled in the art, including the mixed anhidride technique, e.g. that disclosed in U.S. Pat. No. 3,989,812, issued Nov. 2, 1976, to Barrett et al.

Iodination is most conveniently carried out by the Chloramine T reaction, although other oxidation techniques are also well known. See, for example, Chervu, supra, incorporated herein by reference.

The method of use of the compounds of the present invention, both as tracer and as standard, in conventional radioassay techniques, will be readily apparent to the skilled in the art. The standard, which may be folic acid-histamine conjugate of the present invention, or may be N,5-methyltetrahydrofolic acid or folic acid per se, is generally prepared by the type of procedure known in the art wherein standard samples are prepared having various concentrations of the standard. The standard and patient samples are each mixed with a buffer, and the resulting buffered solutions are then normally heated or otherwise appropriately treated to release folates from any binders in the serums, red blood cells or other biological liquids being tested. After cooling to room temperature, the tracer solution and the binder are mixed with the standard and samples, and the mixtures are incubated for a sufficient amount of time to permit completion of binding of the tracer and other folates in the various tubes. This incubation is preferably conducted at a pH range which depends primarily on the type of standard being used. When N,5-methyltetrahydrofolic acid is the standard, the pH range is not critical, and preferably approximately matches the pH of the biological fluid being employed, preferably a pH of about 6.5 to 8.5. When folic acid is the standard, however, the pH is highly critical, and must be within the narrow range of about 9.2 to 9.4. The incubation is conducted at a temperature of 0° to 50° C., most preferably about 15° to 25° C. After the completion of incubation, the bound folates are separated from the free folates, e.g., by adsorption with a suitable adsorbent, e.g., a charcoal adsorbent. The supernatant (bound) folates are determined by counting in a gamma counter, generally for a period of one minute per tube at the usual counting efficiencies of 50 to 80%. A standard curve is prepared, e.g., by plotting the average net counts for each standard against the corresponding concentration of folic acid in ng/ml for each standard tube, and the concentration of folate in the sample tubes containing the biological liquid being analyzed is determined by interpolation from the standard curve.

In a particularly advantageous embodiment of the present invention, there is provided a kit for the entire assay of folate samples, which kit includes a folate assay buffer, for maintaining the pH of the desired level for comparability of binding between the standard and the folates in the samples to be measured, a folate binder, preferably β-lactoglobulin, the folic acid-histamine conjugate [$^{125}$I] tracer, and the folic acid standards. Preferably the kit also contains other components for the analysis, e.g., a charcoal suspension usable to separate the bound from the free folic acid, and a folate control serum, which comprises a human serum with a nominal folic acid concentration, and which can be used as a separate check on the assay system. Preferably the kit also contains ascorbic acid tablets for preservation of the sera samples prior to and during assay.

The invention will be further clarified with reference to the following illustrative embodiments, which are intended to be exemplary only, and not to limit the scope of the invention.

EXAMPLE I

Synthesis and isolation of folic acid-histamine conjugate.

276 mg of histamine (1.5 mmole) are added to a solution of 440 mg (1 mmole) of folic acid in 50 ml of aqueous 0.05 M sodium carbonate solution. The coupling reagent used is 1-ethyl-3-(3-dimethylamino)propyl carbodiimide, of which 196 mg (1.1 mmole) is added slowly with stirring. The mixture is stirred at room temperature for 18 hours and then lyophilized to remove the water.

50 mg of the reaction mixture is taken up in 5 ml of a solvent comprising ethyl acetate:methanol:2N ammonium hydroxide in the volume ratio of 40:10:6. The conjugate is separated from the rest of the reaction mixture by use of a Sephadex LH-20 column, from which the product is eluted in fractions, first with the ethyl acetate:methanol:2N ammonium hydroxide (40:10:6), followed by methanol:water, at a ratio of 1:10. The eluate is collected in 5 ml fractions, which are monitored for UV absorption at 256 nm, 282 nm and 368 nm. Presence of folates in those fractions which showed UV absorption is confirmed by displacement in a radioassay system for folic acid, and by thin layer chromatography on silica gel plates in solvent systems such as ethyl acetate:methanol:2N $NH_4OH$, 40:10:6, or ethyl acetate:methanol: 2N $NH_4OH$:water, 40:20:6:2.5, or on cellulose plates with solvent systems such as isoamyl alcohol:pyridine:water (7:7:6) or n-propanol:conc $NH_4OH$ (7:3). The thin layer chromatography should show but one spot in each of the several systems. The folic acid-histamine conjugate is obtained in roughly 20% yield, and its presence is confirmed, e.g., by its ability to be iodinated.

EXAMPLE II $^{125}$Iodination of the folic acid-histamine conjugate.

In a reaction vessel, 4.0 mCi of $NaI^{125}$ in 0.1 N sodium hydroxide is diluted in a 0.5 M phosphate buffer (pH 8.0), sufficiently to dilute the radioactive iodine to an approximate activity concentration of 400 μCi/10 μl. To this solution is added 2.5 μg of the folic acid-histamine conjugate in 20 μl of methanol:2N ammonium hydroxide (1:1). Separate reagent solutions of Chloramine T, sodium metabisulfite and potassium iodide are made up by dissolving 200 mg of Chloramine T in 10.0 ml distilled water, dissolving 120 mg of sodium metabisulfite in 5.0 ml of distilled water, and dissolving 40 mg of potassium iodide in 10.0 ml of methanol. Chloramine T (0.01 ml, 200 μg) is added to the reaction vessel, which is then mixed thoroughly and the reaction is permitted to proceed for 30 seconds. Then 0.05 ml (1.2 mg) of sodium metabisulfite and 0.1 ml (400 μg) of potassium iodide are added to the reaction vessel, with mixing.

The reaction mixture is purified by eluting through an absorption column measuring 1 × 45 cm and packed with silica gel packing No. SG60 made by E. Merck (70–230 mesh), at a flow rate of 2 to 2.5 ml per minute. After introducing the reaction mixture to the packed bed, 150 ml of ethyl acetate:methanol:2N ammonium hydroxide (40:10:6) is pumped through the column, and 5 ml fractions are collected after the first 25 ml of eluate. Thereafter, 150 ml of ethyl acetate:methanol:2N ammonium hydroxide: water (40:20:6:2.5) is eluted through the column, and collection of 5 ml fractions is continued.

The iodinated folic acid-histamine conjugate will be eluted from the SG60 column after about 23 to 30 fractions have been collected. The total volume of acceptable iodinated conjugate will amount to about 25 ml. The reaction product can be checked for purity by thin layer chromatography, e.g., on cellulose plates (Analabs microcrystalline cellulose, 250 μ thick) in solvent systems such as n-propanol:conc:ammonium hydroxide (7:3) and isoamyl alcohol:pyridine:water (7:7:6).

EXAMPLE III

Use of the folic acid-histamine conjugate in radioassay.

A radioassay kit for the quantitative determination of serum and red cell folate levels is provided comprising the following reagents:

(a) A borate buffer, comprising an aqueous solution of sodium borate adjusted to a pH of 9.3 (0.2 M borate) containing 0.5% gelatin.

(b) A specific folate binding protein, β-lactoglobulin is supplied in lyophilized form. Sufficient binder is supplied (together with sodium borate buffer incorporated therein), such that on reconstitution with 15 ml of distilled water the binder solution will comprise a 0.2 M borate buffer, pH 9.3, with sufficient β-lactoglobulin to bind greater than 50% of the labeled ligand, in the absence of unlabeled ligand.

(c) The labeled ligand is supplied in a lyophilized form, and contains approximately 2.3 μCi of $^{125}$I-histamine-folic acid conjugate per vial, together with sufficient sodium borate buffer so that on reconstitution with 15 ml of distilled water the tracer will be in 0.2 M borate buffer solution, pH 9.3. This amount of tracer is sufficient so that at 100 μl per sample tube to be counted and 60% counting efficiency, it provides approximately 20,000 CPM at the time of calibration. The iodinated histamine-folic acid conjugate is so stable that the usefulness of such tracers is normally dictated only by the half life of the iodine-125.

(d) Six vials of lyophilized standards may be supplied. Such vials may contain sufficient unlabeled folic acid-histamine conjugate (or N,5-methyltetrahydrofolic or folic acid, where either is used as a standard) such that on reconstitution with exactly 2.0 ml of distilled water the resulting solutions will contain 0.5, 1.0, 2.0, 4.0, 8.0 and 16.0 ng of folic acid-histamine (or other) standard per ml in 0.2 M borate buffer, pH 9.3, together with 0.5% gelatin.

(e) A charcoal suspension in water may be supplied ready for use. This should be mixed well before using.

(f) A control serum, comprising a vial of lyophilized human serum, e.g., to provide a known folic acid concentration of about 4.0 ng/ml, may also be supplied for checking.

(g) A supply of ascorbic acid may also be included in the kit, for preservation of serum or red cell samples, which normally requires about 5 mg/ml of ascorbic acid to stabilize the folate.

The radioassay procedure may be as follows: 16 tubes of glass, polypropylene, or other material suitable for use in radioassay, are used for the standard curve, 2 similar tubes are used for the control serum, and 2 similar tubes are used for each clinical sample to be analyzed. 650 μl of assay buffer is transferred into tubes 1 and 2, which make up the blank tubes, 550 μl of assay buffer are transferred to the tubes 3 and 4, which are used as the zero standard, and 500 μl of assay buffer is transferred into all the remaining tubes. 50 μl of the standard containing 0.5 ng of standard per ml are pipetted into tubes 5 and 6. 50 μl of the standard containing 1.0 ng of standard per ml are pipetted into tubes 7 and 8. Similarly, tubes 9 and 10, 11 and 12, 13 and 14, and 15 and 16 will contain 50 μl of 2.0, 4.0, 8.0 and 16.0 ng of standard (unlabeled folic acid-histamine conjugate or other standard) per ml. 50 μl of the folate control serum is pipetted into tubes 17 and 18. Similarly, 50 μl of each clinical sample is pipetted into each of 2 counting tubes. Each tube is mixed by means of a vortex mixer for 2 to 5 seconds, covered with vented caps, and placed in boiling water bath at 100° C. for 15 minutes. Thereafter they are cooled to room temperature and again mixed thoroughly. 100 μl of the $^{125}$I-folic acid-histamine conjugate tracer solution is pipetted into all tubes, and 100 μl of the binder solution is pipetted into all tubes except tubes 1 and 2. The tubes are all mixed on a vortex mixer for 2 to 5 seconds, and incubated at room temperature for exactly 30 minutes. At the end of this incubation period, 0.5 ml of the stirred charcoal suspension is pipetted to all tubes. Each sample tube is mixed thoroughly and allowed to stand at room temperature for an additional 5 minutes. Thereafter each tube is centifuged at 2000 times gravity for 10 minutes and the supernatant liquids are decanted into corresponding counting tubes numbered in the same manner as the original series. These tubes are counted in a gamma counter, e.g., at a counting time of 1 minute per tube.

Upon completion of the radioassay, the "average net counts" for all tubes and samples is calculated by subtracting the average blank counts from the average counts for such standards and samples. The average net counts for the standards are plotted on semi-logarithmic graph paper against the corresponding concentration of the folic acid-histamine conjugate (or other) standard. Thereafter, the concentration of folate in each sample may be obtained by simply interpolating from the standard curve to the average net count for that sample.

When used as tracers, the labeled folic acid-histamine conjugates of the present invention are far cheaper, easier to use, and more reliable than tritiated folic acid. Moreover, they are more stable than other folic acid derivative tracers, such as the tyrosine derivatives disclosed in U.S. Pat. No. 3,989,812. In fact, an iodinated sample of the folic acid-histamine conjugate, stored in the ethyl acetate:methanol:ammonium hydroxide solvent for a period of seven months, behaved in assay as well as it did when it was freshly prepared, giving a standard curve which was in the same position as one plotted just after preparation of the tracer. Thin layer chromatographic analysis of the product showed less than 10% impurities after that period of time. Similarly, improvements in stability are realized when the folic acid-histamine conjugate is used as the standard.

Preferably the folic acid-histamine conjugate is used both unlabeled, as a standard, and labeled, as the tracer, in the same radioassay. Thus instead of having two different bindable species, e.g., a folic acid standard and a conjugated folic acid-histamine tracer, being used to estimate levels of the yet further different species of N,5-methyltetrahydrofolic acid, both the standard and the tracer are basically the same compound, the only difference being the inclusion of an iodine atom on a portion of the molecule remote from the binding site.

The specific embodiments described herein are meant to be exemplary only, and various modifications will be apparent to those skilled in the art from reading the present specification, or from practice of the disclosed invention. It is intended to cover all such modifications as fall within the spirit and scope of the invention.

I claim:

1. A chemical compound of the formula:

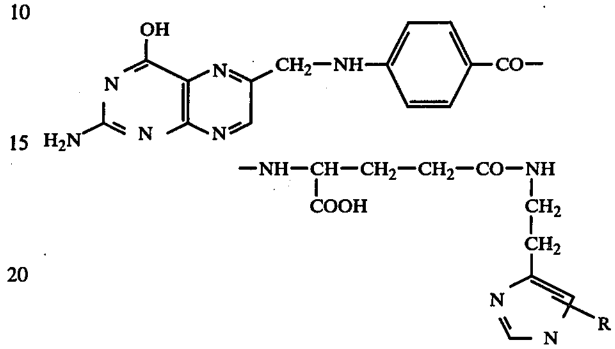

wherein R is selected from the group of H, $^{125}$I, and $^{131}$I.

2. The compound of claim 1 in which R is H.

3. The compound in accordance with claim 1 wherein R is $^{125}$I.

4. A tracer composition for radioassaying biological samples, comprising an iodinated conjugate of folic acid and histamine.

5. The composition of claim 4, further comprising an alkaline buffer agent.

6. A composition for use in radioassay analysis for folic acid, metabolites of folic acid, derivatives of folic acid, or mixtures thereof, comprising a folic acid-histamine conjugate.

7. The composition of claim 6, further comprising a radioactive tracer material attached to said conjugate.

8. The composition of claim 7, wherein the radioactive tracer material comprises an iodinated conjugate of folic acid and histamine.

9. The composition of claim 6, for use as a standard in said analysis, said standard consisting essentially of a folic acid-histamine conjugate.

10. A method for analyzing a sample for the presence of a folic acid compound selected from the group of folic acid, a metabolite of folic acid, a derivative of folic acid, or mixtures thereof, comprising mixing said sample with a preselected amount of a labeled compound of the chemical formula:

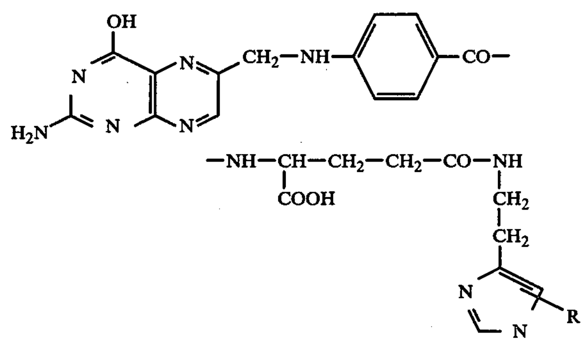

wherein R is $^{125}$I or $^{131}$I in the presence of a folate binder to bind at least some of said labeled compound, separating the bound labeled compound from the remaining free labeled compound, and counting the radiation emitted from either the bound labeled compound or the free labeled compound in a gamma counter.

11. The process of claim 10, wherein R is $^{125}I$.

12. The process of claim 10, further comprising forming a second mixture of said labeled compound with a known amount of a standard, which is an unlabeled compound, in the presence of a folate binder to bind at least some of said labeled compound, separating the bound labeled compound from the remaining free labeled compound, measuring the radiation emitted from either the bound labeled compound or the free labeled compound from said second mixture by means of a gamma counter, and determining the amount of said folic acid compound by comparing the radioactivity of the bound or unbound labeled compound from said mixture with the radioactivity of the bound or unbound labeled compound, respectively, from said second mixture.

13. The method of claim 12, wherein said standard is an unlabeled compound having a chemical formula:

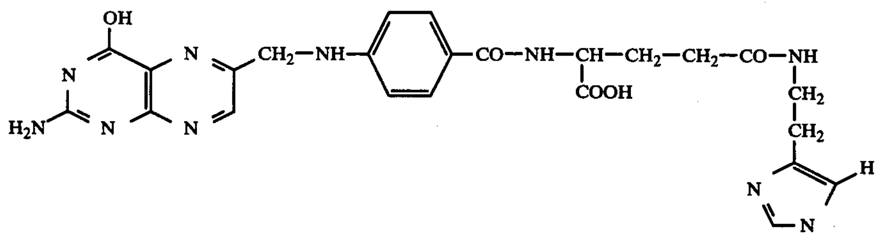

14. The method of claim 12, wherein said standard is unlabeled folic acid.

15. The method of claim 12, wherein said standard is unlabeled N,5-methyltetrahydrofolic acid.

16. An article of manufacture or mercantile unit in the form of a radioassay test kit suitable for analyzing biological liquids for folic acid, N,5-methyltetrahydrofolic acid, metabolites of folic acid, derivative of folic acid, and mixtures thereof, said unit comprising containers or similar articles which contain various chemical components to be used in the analysis, said components comprising a supply of a specific folate binder, a radioactive tracer having the chemical formula:

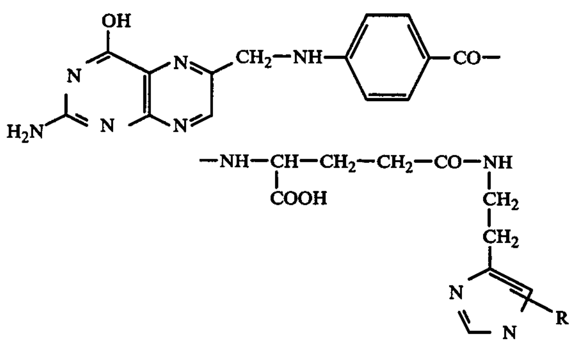

wherein R is $^{125}I$ or $^{131}I$, and a supply of standard compound, said containers being packaged together in said unit.

17. The kit of claim 16, wherein the standard compound is a conjugate of folic acid and histamine.

18. The kit of claim 16, wherein the standard compound is folic acid.

19. The kit of claim 16, further comprising a charcoal suspension.

20. The kit of claim 16, further comprising a supply of buffering material.

21. The kit of claim 16, further comprising a supply of ascorbic acid.

22. A method for analyzing a sample for the presence of a folic acid compound selected from the group of folic acid, a metabolite of folic acid, a derivative of folic acid, or mixtures thereof, comprising mixing said sample with a preselected amount of a labeled compound that is an iodinated conjugate of folic acid and histamine in the presence of a folate binder to bind at least some of said labeled compound, separating the bound labeled compound from the remaining free labeled compound, and counting the radiation emitted from either the bound labeled compound or the free labeled compound in a gamma counter.

23. The process of claim 22, further comprising forming a second mixture of said labeled compound with a known amount of a standard, which is an unlabeled compound, in the presence of a folate binder to bind at least some of said labeled compound, separating the bound labeled compound from the remaining free labeled compound, measuring the radiation emitted from either the bound labeled compound or the free labeled compound from said second mixture by means of a gamma counter, and determining the amount of said folic acid compound by comparing the radioactivity of the bound or unbound labeled compound from said mixture with the radioactivity of the bound or unbound labeled compound, respectively, from said second mixture.

24. The method of claim 23, wherein said standard is an unlabeled compound having a chemical formula:

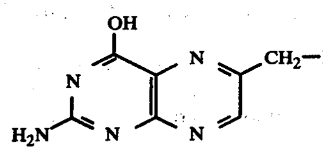
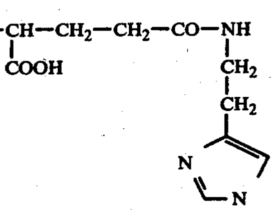

25. The method of claim 23, wherein said standard is unlabeled folic acid.

26. The method of claim 23, wherein said standard is unlabeled N,5-methyltetrahydrofolic acid.

27. An article of manufacture or mercantile unit in the form of a radioassay test kit suitable for analyzing biological liquids for folic acid, N,5-methyltetrahydrofolic acid, metabolites of folic acid, derivative of folic acid, and mixtures thereof, said unit comprising containers or similar articles which contain various chemical components to be used in the analysis, said components comprising a supply of a specific folate binder, a radioactive tracer that is an iodinated conjugate of folic acid and histamine, and a supply of standard compound, said containers being packaged together in said unit.

28. The kit of claim 27, wherein the standard compound is a conjugate of folic acid and histamine.

29. The kit of claim 27, wherein the standard compound is folic acid.

30. The kit of claim 27, further comprising a charcoal suspension.

31. The kit of claim 27, further comprising a supply of buffering material.

32. The kit of claim 27, further comprising a supply of ascorbic acid.

* * * * *